US008637076B2

(12) United States Patent
Habib et al.

(10) Patent No.: US 8,637,076 B2
(45) Date of Patent: *Jan. 28, 2014

(54) PREDNISOLONE SALT FORMULATIONS

(75) Inventors: Walid Habib, Maple Grove, MN (US);
Bhaveshkumar Kothari, Smithtown, NY (US)

(73) Assignee: Cima Labs Inc., Brooklyn Park, MN (US)

( * ) Notice: Subject to any disclaimer, the term of this patent is extended or adjusted under 35 U.S.C. 154(b) by 1276 days.

This patent is subject to a terminal disclaimer.

(21) Appl. No.: 11/638,216

(22) Filed: Dec. 13, 2006

(65) Prior Publication Data

US 2007/0281013 A1    Dec. 6, 2007

Related U.S. Application Data

(60) Provisional application No. 60/810,015, filed on Jun. 1, 2006.

(51) Int. Cl.
*A61K 9/46* (2006.01)

(52) U.S. Cl.
USPC .......................................................... 424/466

(58) Field of Classification Search
USPC .......................................................... 424/466
See application file for complete search history.

(56) References Cited

U.S. PATENT DOCUMENTS

| | | | |
|---|---|---|---|
| 2,909,522 A | 10/1959 | Hitchings et al. | |
| 3,921,636 A | 11/1975 | Zaffaroni | |
| 4,303,643 A | 12/1981 | Armstrong | |
| 4,393,200 A | 7/1983 | Miyashita et al. | |
| 4,966,770 A | 10/1990 | Giannini et al. | |
| 5,141,961 A | 8/1992 | Coapman | |
| 5,154,926 A | 10/1992 | Kawasaki et al. | |
| 5,178,878 A | 1/1993 | Wehling et al. | |
| 5,223,264 A | 6/1993 | Wehling et al. | |
| 5,234,957 A | 8/1993 | Mantelle | |
| 5,455,049 A | 10/1995 | Anaebonam et al. | |
| 5,496,541 A | 3/1996 | Cutler | |
| 5,503,846 A | 4/1996 | Wehling et al. | |
| 5,516,524 A | 5/1996 | Kais et al. | |
| 5,607,697 A | 3/1997 | Alkire et al. | |
| 5,763,449 A | 6/1998 | Anaebonam et al. | |
| 5,780,055 A * | 7/1998 | Habib et al. | 424/464 |
| 5,962,461 A | 10/1999 | Anaebonam et al. | |
| 6,024,981 A | 2/2000 | Khankari et al. | |
| 6,221,392 B1 | 4/2001 | Khankari et al. | |
| 6,740,341 B1 * | 5/2004 | Holt et al. | 424/490 |
| 6,767,557 B2 | 7/2004 | Ulrich et al. | |
| 2002/0197327 A1 | 12/2002 | Ulrich et al. | |
| 2003/0096791 A1 * | 5/2003 | Gupte et al. | 514/57 |
| 2003/0118654 A1 | 6/2003 | Santos et al. | |
| 2003/0161888 A1 | 8/2003 | Fernandez et al. | |
| 2004/0161459 A1 * | 8/2004 | Do et al. | 424/465 |
| 2004/0265375 A1 | 12/2004 | Platteeuw et al. | |
| 2005/0118258 A1 * | 6/2005 | Shroppolo et al. | 424/464 |
| 2005/0287211 A1 | 12/2005 | Yoshida et al. | |

FOREIGN PATENT DOCUMENTS

| | | |
|---|---|---|
| BE | 615854 | 10/1962 |
| EP | 0052085 | 5/1982 |
| WO | 95/19759 | 7/1995 |
| WO | 00/30617 | 6/2000 |
| WO | 03/053415 | 7/2003 |
| WO | 2004/022037 | 3/2004 |
| WO | 2004/060354 | 7/2004 |

OTHER PUBLICATIONS

Berthold et al.; "Preparation and Characterization of Chitosan Microspheres as Drug Carrier for Prednisolone Sodium Phosphate as Model for Anti-Inflammatory Drugs"; Journal of Controlled Release; 1996; vol. 39; pp. 17-25.
Drugs.com; "BioMarin Announces U.S. FDA Acceptance of Orapred ODT Filing"; New Drug Applications [Online]; Oct. 19, 2005; URL: http://www.drugs.com/nda/orapred_odt_051019.html.
Ahmed et al.; "Bioavailability and Pharmacokinetics of a New Liquid Prednisolone Formulation in Comparison with Two Commercially Available Liquid Prednisolone Products"; Current Therapeutic Research; Jul. 2001; vol. 62, No. 7; pp. 548-556.
Hendeles; "Selecting a Systemic Corticosteroid for Acute Asthma in Young Children"; The Journal of Pediatrics; Feb. 2003; vol. 142; pp. S40-S44.
Gomez Gallardo; International Search Report in PCT/US07/13008; Jan. 3, 2008; 4 pages; European Patent Office; Rijswijk, Netherlands.
Ellen Moyse; International Preliminary Report on Patentability in PCT/US07/13008; Dec. 3, 2008; 9 pages; International Bureau of WIPO; Geneva, Switzerland.
Gomez Gallardo; Written Opinion of the International Searching Authority in PCT/US07/13008; Dec. 1, 2008; 8 pages; European Patent Office; Rijswijk, Netherlands.

\* cited by examiner

*Primary Examiner* — Frederick Krass
*Assistant Examiner* — Adam C Milligan
(74) *Attorney, Agent, or Firm* — Banner & Witcoff, Ltd.

(57) ABSTRACT

The present invention relates to tablets containing prednisolone salts and in particular prednisolone sodium phosphates. The dosage forms include ODTs and non-ODTs, effervescent tablets and noneffervescent tablets and tablets meeting certain performance criteria.

10 Claims, No Drawings

PREDNISOLONE SALT FORMULATIONS

This application claims priority from U.S. Provisional Patent Application No. 60/810,015, filed on Jun. 1, 2006, the disclosure of which is hereby incorporated by reference in its entirety.

BACKGROUND OF THE INVENTION

There are many known and successful techniques for providing taste masked dosage forms including taste masked orally disintegrable and/or dissolvable dosage forms ("ODT"). These techniques include a number which are owned by the assignee, CIMA LABS INC., 10000 Valley View Rd, Eden Prairie Minn., such as U.S. Pat. Nos. 5,178,878 and 5,223,264, which describe taste masked ODTs produced using, inter alia, a protected particle and effervescents. See also U.S. Pat. Nos. 5,503,846, 5,607,697, and 6,024,981.

Another generally successful technique is described in CIMA's U.S. Pat. No. 6,740,341. That patent describes a dual coating system used for particularly objectionable drugs which included a spacing layer overcoating a granulate, followed by the application of an overcoating layer of a taste masking material. The spacing layer helps prevent puncture or compromise of the taste masking layer particularly by sharp or jagged crystalline materials. The examples describe a spacing layer composed of 20% by weight gain or more of ethyl cellulose and PVP or ethyl cellulose and HPMC. See also Kais et al., U.S. Pat. No. 5,516,524.

While CIMA's techniques have been highly successful in a technical sense, there are nonetheless situations and drugs where further development is necessary to obtain adequate performance in terms of construction, taste masking performance and drug delivery. One such particularly challenging drug is prednisolone. The sodium phosphate salt (a term which includes any sodium and phosphate containing salt such as, without limitation, prednisolone disodium phosphate, unless otherwise indicated.) of this drug is known to be used to treat a vast array of conditions including: allergic states, dermatologic diseases, endocrine disorders, neoplastic disorders, and rheumatic disorders and the acetate salt is known for use in ophthalmic preparations. Products are also currently available using the free base material in a traditional swallow tablet or in a liquid.

While the free base form of prednisolone is objectionable tasting, it is not so objectionable that its taste cannot be managed by fairly routine techniques. However, it does present solubility and bioavailability problems. Prednisolone sodium phosphate has good solubility and bioavailability. But its taste is abysmal—far more than many taste masking strategies can handle. Indeed, it is believed that, in no small measure because of its aggressively objectionable flavor, prednisolone salts and, in particular, the sodium phosphate salt, are not only not available as ODT tablets, they are not available as tablets at all. The only dosage form that is available for this particular drug salt is a liquid where its objectionable flavor can be diluted—indeed drowned—by conventional sweeteners, flavorings and other masking techniques.

The sheer volume of the materials required to provide adequate taste masking in a liquid would suggest to formulators that any tablet formulation, let alone an ODT which is intended to dissolve/disintegrate in the mouth, is unattainable. While the volume of liquid that constitutes a dose can vary widely, tablets can only be so big. Too large a tablet or too many tablets would not be accepted in the marketplace. Tablets of greater than about 1 gram are rare and pose significant problems to many who are squeamish about swallowing, including children and the elderly. Thus, the multiple demands made of tablets in terms of excipients, the amount of active, processability, and size significantly limit the availability and room for many traditional taste masking strategies in solid tablets. And with a material as bad tasting as this, it is no wonder only a liquid form exists.

SUMMARY OF THE INVENTION

In one embodiment, the present invention provides a taste-masked orally dissolving dosage form of a prednisolone salt and in one embodiment, the sodium phosphate salt. In one aspect of the invention, there is provided an orally disintegrable/dissolvable tablet comprising rapid release active pharmaceutical ingredient ("API") -containing particles (often referred to merely as "API-containing particles"), an effervescent couple and at least one excipient. The API-containing particles themselves comprise carrier particles coated with a layer of a prednisolone salt (also known as the API-containing layer), the prednisolone salt being present in an amount of about 20 to about 45% by weight of the API-containing particle (the final particle weight with all coatings). In some embodiments, the now API-containing layer coated carrier particle is itself overcoated. In preferred embodiments, at least twice, by two entirely different types of coatings. First, the prednisolone salt containing layer is overcoated with a seal coating layer which is present in an amount of about 2% to about 15%.

This now seal coated particle is itself overcoated with a taste masking layer which is present in the finished particle in an amount of about 25% to about 55%. The API-containing particle (carrier, API-containing layer and at least the two overcoating layers just discussed) is present in the finished tablet in an amount of about 55% to about 75% by weight of the tablet. The effervescent couple may be present in an amount of about 5% to about 25% percent by weight of said tablet, and the balance is made up of at least one excipient. In another aspect of the invention, the seal coating layer and the taste masking layer are coordinated such that the application of the taste masking layer will not adversely affect the seal coating layer.

In one embodiment, the tablets of the present invention may have a hardness of about 8 to about 20 Newtons. In other embodiments, the tablets may have a hardness of about 8-12 Newtons, about 10-14 Newtons, or about 14-18 Newtons. In still other embodiments, the tablets have a harndess of about 15 Newtons or more, more preferably 20 Newtons or more, and a friability, as measured by the USP 26th revision (Jan. 1, 2003), at the time of filing, of about 2% or less. In yet another embodiment, these tablets may include at least one non-direct compression carbohydrate (sugar, sugar alcohol, etc.) as a filler. See U.S. Pat. No. 6,024,981. Preferably, these tablets are capable of rapidly disintegrating/dissolving in a patient's mouth in about 60 seconds or less, more preferably about 30 seconds or less, such that the rapid release API-containing particles can be swallowed as a dispersion, suspension or slurry. These tablets may be packaged in blister packages or in openable and reclosable multi-tablet packages.

The tablets of another embodiment of the invention may have a hardness of about 20 Newtons or less, and a friability of more than 2% as measured by the U.S.P. method as of the filing date. In some embodiments, they are capable of rapidly disintegrating/dissolving in a patient's mouth in about 60 seconds or less, more preferably about 30 seconds or less, such that the rapid release API-containing particles can be swallowed as a dispersion, suspension or slurry. Preferably, during the dissolution/disintegration and ingestion of the tablet, it provides a pleasant organoleptic sensation. These tablets are often packaged in a blister package.

The tablets in accordance with this aspect of the present invention are "ODT" tablets (defined here as "orally disintegrable/dissolvable tablets"). "Disintegrable/dissolvable" means that at least a portion of the dosage form may disintegrate and/or dissolve when placed on the tongue in a patient's mouth. This term does not include tablets which are designed to facilitate transfer of an API across an oral mucosa such as sublingual or buccal tablets. When disintegration/dissolution of the effervescent couple and soluble excipients occurs, the resulting dispersion, suspension or solution is swallowed.

Given the aggressive and offensive taste of prednisolone sodium phosphate, it is easy to speculate as to why no solid dosage forms currently exist. One would think that contemplating an ODT tablet of this salt is merely tempting the fates as to adequately work it must disintegrate and/or dissolve in the mouth. This means, of course, that the length of time that the drug resides in the mouth is far in excess of the amount of time necessary in a traditional swallow tablet. And with something this aggressive, seconds may count. Indeed, other than for the challenge, one would not be alone in wondering why even bother with an ODT. The fact that one could be successfully made is therefore remarkable. Indeed, the fact that one would even try is remarkable.

In another embodiment of the present invention, the API-containing particles are "rapid release" particles. By "rapid release" it is meant that once the particles have entered the stomach, the API is generally as available as a liquid form of the same active. The ODTs in accordance with this aspect of the invention should be, in short, "bioequivalent," as that term is defined in 21 U.S.C. and 21 C.F.R. as of the filing of this document when compared to the currently marketed liquid of prednisolone sodium phosphate. [This requires that the coatings used be selected such that they are sufficiently functional within the mouth to protect the taste buds and yet get out of the way sufficiently quickly thereafter so as to allow the body to use the active as if it were, in essence, uncoated.]

The invention also includes methods of administering dosage forms in accordance with the present invention which include the steps of placing a tablet in accordance with the invention into a patients mouth in need of prednisolone, allowing the tablet to disintegrate and/or dissolve in the mouth substantially on the tongue (as opposed to sublingual or buccal) to form a dispersion, suspension or slurry including the API-containing particles, and swallowing the resulting dispersion, suspension or slurry of API-containing particles.

Also considered part of the invention is a method of making tablets in accordance with the present invention which include the steps of: coating prednisolone sodium phosphate onto a sugar sphere to form an API-containing layer, selecting a seal coating material and a coordinated taste masking material; forming a seal coating layer substantially coating said API-containing layer; forming a taste masking layer substantially coating said seal coating layer to form a an API-containing particle, blending said API-containing particle with an effervescent couple and an excipient, and compressing the resulting blend to form a tablet.

In another aspect, the invention provides a tablet comprising: rapid release API-containing particles, and an excipient. The API-containing particles comprise carrier particles coated with an API-containing layer of a prednisolone sodium phosphate present in an amount of about 20 to about 45% by weight of the API-containing particles. The API-containing layer is overcoated with a seal coating layer present in an amount of about 2% to about 15% by weight, and the seal coating layer being overcoated with a taste masking coating layer present in an amount of about 25% to about 55% by weight gain. The API-containing particles are present in an amount of about 55% to about 75% by weight of said tablet. This tablet could be effervescent or could be a non-effervescent tablet. The tablet is preferably an ODT tablet, but it is not necessarily an ODT tablet.

Also contemplated as a separate aspect of the invention are tablets comprising prednisolone sodium phosphate in an amount of about 13.4, about 20.2 or about 40.3 mg and an excipient. These tablets could be effervescent or could be non-effervescent tablets. They are preferably ODT tablets, but they are not necessarily ODT tablets.

In still another aspect of the invention, there are provided rapid release taste masked orally dissolving dosage forms. In certain embodiments, the dosage forms comprise API-containing particles comprising: a carrier particle coated with an API-containing layer of a prednisolone sodium phosphate, said prednisolone sodium phosphate being present in an amount of about 20 to about 45% by weight of said API-containing particle, said API-containing layer overcoated with a seal coating layer present in an amount of about 2% to about 15% by weight, and said seal coating layer being overcoated with a taste masking coating layer present in an amount of about 25% to about 55% by weight gain.

DETAILED DESCRIPTION OF THE INVENTION

Throughout the entire specification, including the claims, the word "comprise" and variations of the word, such as "comprising" and "comprises," as well as "have," "having," "includes," "include" and "including," and variations thereof, means that the named steps, elements or materials to which it refers, but other steps, elements or materials may be added and still form a construct within the scope of the claim or disclosure. When recited in describing the invention and in a claim, it means that the invention and what is claimed is considered to what follows and potentially more. These terms, particularly when applied to claims, are inclusive or open-ended and do not exclude additional, unrecited elements or methods steps. The term "between" as used in connection with a range includes the endpoints unless the context suggests otherwise. All references to testing is at room temperature (20-25° C.) unless otherwise specified and all references to temperature are in degrees centigrade unless otherwise specified.

In the present context, "consisting essentially of" is meant to exclude any API, coating, excipient or combination of excipients or, as appropriate, any amount of any of the foregoing that would alter the basic and novel characteristics of the invention.

There are many strategies that could be considered in an attempt to solve the diverse problems that a prednisolone sodium phosphate, and in particular, an ODT version of a prednisolone sodium phosphate tablet poses. Merely wrapping an objectionable material in a generally impenetrable enteric coating that would remain in tact until the very high basic pH of the intestines are implicated would certainly be easy. But this API needs to be dissolved in the stomach. A single layer coating system such as, for example, the use of Eudragit E-100 could also be considered. However, this is inadequate also. While prednisolone salts prepared as described herein do not threaten to puncture or otherwise physically compromise a taste masking coating of (the problem solved in the '341 patent) with time, the API salt is believed to be capable of migrating into and indeed across such a layer.

Perhaps the problem could be solved by a particularly thick taste masking coating layer. However, with the increase in thickness of the coating material comes an increase in the size and weight of the particle which can dramatically limit the overall quantity of prednisolone salt, not only in the particle, but in the finished tablet as well.

And, not all potential materials useful as seal coatings are applicable. Given the restrictions on size and dose load, coating would have to be accomplished using a relatively thin coating of material which both provided taste masking and did not appreciably interfere with the availability of the prednisolone salt, i.e., will be bioequivalent to the currently available liquid dosage form. But these are not the only limitations on the materials that can be used for the seal coating.

In the '341 patent, there are two examples using two coatings. Example 1 has a 20% weight gain spacing layer and a 30% taste masking layer. Example 2 has a 50% spacing layer and a 70% weight gain taste masking layer. Using spacing layers of this thickness can provide certain processing advantages where the use of thinner layers could pose obstacles. For example, in accordance with the present invention, the seal coating layer may need to be dissolved in one solvent and be insoluble in the solvent used for the taste masking layer to ensure that the seal coating layer's properties are not altered during the application of the taste masking layer. If the seal coating layer were thicker, even if it was somewhat solubilized during the application of the taste masking layer, the coating could be sufficiently thick so that taste masking was not compromised. However, at that thickness, the API loading of the particles and bioequivalency could be adversely affected.

In one embodiment of the present invention which includes a seal layer, the seal coating layer is produced from a material which is dissolved, suspended or dispersed in water and the taste masking layer is produced from a material which is dissolved, suspended or dispersed in alcohol. In another embodiment, the seal coating material is water soluble and the taste masking layer is composed of something that is generally insoluble in water. As should be apparent, it is not merely enough to pick materials for these two layers based on their respective ability to form a seal or taste masking coating. They must be "coordinated" such that the application of the taste masking layer, in the restricted thickness described, will not adversely affect the very thin seal coating.

Another aspect of some of the embodiments of the present invention is a dosage form which not only provides adequate taste masking and is an ODT but also provides a pleasant organoleptic sensation. This means that the tablet is not objectionably gritty or sandy during dissolution and/or disintegration and provides a dispersion, slurry or suspension which can be swallowed, generally as a mass of the undissolved API-containing particles, which a patient would not find objectionable. Of course, the shape and composition of the coated particle can be important as is the amount of effervescent material, the selection of the types and amounts of excipients and the use of flavors and the like.

Note that the coated particles of the present invention should not themselves dissolve or disintegrate in the mouth to an extent which would compromise their taste masking ability. These particles will be dispersed, suspended or slurried in the mouth and swallowed. But if the API-containing particles' coatings are unpalatable either in terms of taste or texture, if depending upon their shape, the particles may not move as a mass and may distribute themselves throughout the mouth under the tongue, between the cheek and gums, etc., the entire experience of taking the tablet could be unpleasant. To be clear, the ODT tablets of the invention preferably include both water soluble and non-rapidly water soluble or even water insoluble elements. The tablets may include, as an example, an insoluble excipient, the coated particle described herein which are possibly eventually soluble, but should not be appreciably soluble in the time period that the tablet is in the mouth, and freely soluble materials such as certain sugars. Once the ODT tablet is placed in the mouth, some of the materials will begin to dissolve. This process contributes to the disintegration of the tablet. An effervescent couple, if present, will react and the release of gas will cause further disintegration, which increases the surface area and the dissolution as well. Eventually, there will be bits of yet to be dissolved water soluble materials, anything that is insoluble and the API-containing particles to be swallowed as a suspension, dispersion or slurry with the now dissolved portions of the tablet.

Particle size and particle size distribution may also be important to certain embodiments of the invention. Accordingly, it is preferred that the API-containing particles are sized such that at least 90% of them would pass through a 30 mesh screen, more preferably 95%, most preferably 98% or more would pass through a 30 mesh screen. Particles which are too fine, however, are difficult to maintain in a cohesive suspension or slurry and may present content uniformity and processing issues. Accordingly, it is also desirable that not less than about 60% of the coated API-containing particles be retained on a 60 mesh screen, more preferably at least about 65% be retained thereon. And finally, it is preferable that not more than 40% of the particles be collected in a pan once being passed through a 60 mesh screen, and more preferably not more than 30% be collected in a pan. These numbers are, of course, by weight. And, the need to stay within such a tight particle size distribution also has an effect on the amount of coating materials which can be used to provide taste masking as does the need to provide an adequate load of active in the particles. From these often competing and mutually exclusive criteria, one can appreciate just how difficult designing a dosage form for a prednisolone salt containing ODT can be.

And as if the foregoing is not complicated enough, moisture and impurities can have a dramatic effect on the construction of tablets in accordance with the present invention. Conventional raw prednisolone salt API can have up to about 3% of impurities and up to about 6.5% moisture. The processes of coating the API-containing layer onto the carrier particle as well as the overcoating steps also introduce water and/or other solvents, all of which can reduce the effective load of actual API. Indeed, it was found that unless the API was assayed and its water level and impurity level accounted for and compensated for by additional API, it was difficult to obtain a final tablet containing the necessary content of active while meeting all of the other criteria discussed herein.

Moreover, a moisture content in excess of about 5% can cause undesirable changes to the active ingredient which is itself water soluble. The drug can become disassociated from its salt which can affect its solubility and bioavailability and could render the resulting dosage form nonbioequivalent. Degradation could also occur which would affect the potency of the dosage form as well as providing potentially undesirable side products. The final dosage forms in accordance with the present invention preferably have a total moisture content of less than about 5% by weight of the final API-containing particles, more preferably an amount less than 4% and most preferably an amount less than 3% by weight of the total dosage form.

With all of the foregoing in mind, in accordance with one aspect of the invention, and for tablets including API-containing particles, the API-containing particles of the present invention generally begin with a carrier particle. A solid support or carrier particle in accordance with the present invention can be composed of any material useful for layering in accordance with this and other conventional pharmaceutical applications. These can include, without limitation, particles, crystals, granulates, capsules, mini-tablets microparticles, microgranules, microcrystals or microcapsules. Particles, granules and crystals have their traditional meaning. "Capsule" in accordance with the present invention includes generally hollow, spherical vessels such as liposomes, micelles and the like. These may be dried. Carrier particles can be composed of any number of materials or mixtures thereof including particles created from one or more of the taste masking materials, polymers, solid dicalcium phosphate and the like. However, in a preferred embodiment, the carrier particles are made of a sugar. "Sugar" in accordance with the present invention generally includes other forms of carbohydrate such as, for example, sugars, sugar alcohols, ketoses, saccharides, polysaccharides, oligosaccharides and the like, as well as celluloses and modified celluloses. These include, without limitation, sucrose, mannitol (spray dried and granular) lactose, and microcrystalline cellulose. Most preferred in accordance with the present invention are sucrose and microcrystalline cellulose. Useful sucrose spheres are available from Paulaur corporation, 105 Melrich Road, Cranbury, N.J. 08512. Useful microcrystalline spheres are sold by Asahi Kasei Chemicals Corp, with the following address: Hibiya-Mitsui Building 1-2 Yurakucho 1-chome, Chiyoda-ku, Tokyo 100-8440 Japan under the designation CELPHERES.

The size of the carrier particles can vary considerably with, amongst other things, the application, volume of the carrier particles that will be used in the formulation, the type of dosage form in which it will be included, and the thicknesses of the layers that will coat it. Carrier particles that are too small can be difficult to coat. Carrier particles that are too large can be difficult to work with, can affect content uniformity and can provide an unpleasant organoleptic sensation in the mouth. Of course, the larger the particle size, the smaller the surface area of the API that will be provided in the mouth thus reducing the potential exposure to the taste buds and other sensory organs within the mouth, further enhancing taste masking.

In accordance with the present invention, the carrier particle size is preferably between about 10 microns and about 1,000 microns, more preferably between about 20 microns and 600 microns. This means that at least about 90% of the carrier particles, by weight, fall within these ranges based on sieving. In a more preferred embodiment, the carrier particles will predominantly have more than 50% fall within a 60 to 80 mesh screen cut. More particularly, the amount by weight greater than 300 µm is about 0%, the amount by weight greater than 250 µm is less than about 10%, the amount in between about 180 and about 250 µm is about 90% or more, and the amount by weight less than 180 µm is about 10% or less.

"Micro" in the context of carrier particles means a carrier particle having a particle size of below about 50 microns. Preferably the carrier particles are substantially spherical although the particle dimensions can vary and can be, without limitation, elliptical, generally egg-shaped, rod-shaped, regular and/or irregularly shaped.

Covering at least a portion of the carrier particle is at least one API-containing layer. In a particularly preferred embodiment, the prednisolone salt is prednisolone sodium phosphate. The amount of prednisolone sodium phosphate present in a dose (which can consist of one or more, but preferably no more than two tablets) will vary depending upon a number of factors including the patient, the patient's condition, the length and extent of administration, the salt form used, and a doctor's sound medical judgment. However, generally, each dose of prednisolone (measured as the free base) ranges from between about 0.10 micrograms and about 2 grams, preferably between about 0.50 micrograms and about 1 gram per dosage form (e.g., tablet, teaspoonful, etc.), most preferably 1, 2.5, 5, 10, 15 and 30 milligrams per dose (generally dosed up to 4 times a day for a total daily dose of between about 4 and about 130 milligrams).

By "covering at least a portion" in context of any coating layer described, it is understood that the complete surface area of each carrier particle or coated particle need not be covered. Indeed, while the efficiency of the system is improved considerably by the use of a substantially complete and uniform coating, it is not required that, for example, the prednisolone salt coating cover even a majority of the carrier particles or a majority of the surface area of the carrier particles. Preferably, however, the API-containing layer covers substantially all of the carrier particles to which it is applied (it is possible to mix some coated and uncoated solid support if desired) and each successive layer preferably does the same. By "substantially all" it is understood that, generally speaking, the API-containing layer increases the weight of the carrier particle by at least about 40%, more preferably at least about 50%, and most preferably at least about 55% w/w relative to the weight of the uncoated carrier particles. Note that the API-containing layer is preferably assayed and weighed so that the weight gain of the prednisolone salt reported is accurate. Successive layers are based on calculated target levels of desired weight gain based on the weight of the dry ingredients (w/w). Thus, the amount of the sealing layer is based on a calculated target increase in weight, for example 10% compared to the measured weight of the carrier particle coated with the API-containing layer. It should be understood that this means that in producing the coated particle, an amount of seal coating material used is a calculated amount which should be sufficient to provide, staying with the same illustration, a 10% w/w seal coating (weight gain) when applied. It will be appreciated that the actual coating level may or may not meet the target depending upon a number of factors including, without limitation, the nature of the coating process, the length of coating application, the coating material, the moisture content and the like. While it would be expected that coating efficiency will generally be less than 100% and thus the amount of actual coating will be less than the target, because of the factors just described, and possibly others, the actual coating layer could be present in an amount that is ±about 30% of the target calculated weight gain. This can be confirmed, if needed, by weighing the particles after seal coating and subtracting from that number the weight of the API layer coated carrier particle. The result will be the weight of the seal coating material actually applied. This, in turn, is compared to the amount of coating material calculated and used. The difference should not be more than about 30%.

If the target is not close to the endpoints of the range described, and/or where there is prior experience with a particular coating system one can be reasonably assured that the target has been meet, or at least that the result is in the described range, even if not confirmed by actual weight. While the forgoing has been described in terms of the sealing layer, it applies equally to the taste masking layer, however, the comparison in that instance is between the weight of the taste masking coated API-containing particle with the seal coated particle. Again, it need not be necessary to actually weigh the particle to confirm the degree of coating depending upon prior experience or where the target is not within 30% of the end of the described ranges.

When, in this document, a reference is made to weight gain, target weight gain, w/w or degree of coating of the seal and/or taste masking coating layers, or words to that effect, it is contemplated that the above methodology should be employed.

In the finished API-containing particles, the total amount of prednisolone sodium phosphate salt, measured as the percent by weight of the salt, ranges from about 20 to about 45%, more preferably about 29 to about 36% and even more preferably about 31 to about 34% by weight of the finished particles.

The API-containing layer, and indeed the overcoating layers as well, can be applied by any conventional coating process such as use of a Wurster fluidized bed where the coating material enters from the bottom of the reactor. The API, the prednisolone salt, is preferably dissolved, suspended or dispersed in a solvent and the resulting solution, dispersion or suspension is then coated onto the surface of the carrier particles preferably in a way which provides a substantially homogeneous coating. The solvent should be acceptable to the U.S. Food and Drug Administration or comparable government agencies and is sufficiently volatile to be removed quickly either by air drying or by use of other drying equipment at a temperature which is insufficient to cause damage to the API. The concentration of the API in the solvent will vary with the solvent, the prednisolone salt used, and whether or not a solution, suspension or dispersion is to be produced. It is understood, however, that as little solvent as is necessary should be used. Solvents in accordance with the present invention include, for example, water, alcohol, dehydrated ethanol, methanol, isopropyl alcohol, acetone, dioxane and chloroform. The API-containing solution, suspension or dispersion is to be applied such that the weight gain of the carrier particle is at least about 40% as previously discussed based on the weight of the carrier particle. The weight gain and API content can be determined by weighing and assay.

The seal coat or seal coating layer is applied over top of the API-containing layer. As is true with the API-containing layer, it need not coat all of the particles nor any one particle completely but substantially coated is preferred. Because an incomplete seal might allow migration of the prednisolone salt through the taste masking layer and may expose a patient to the taste of the API, the more complete the coating, the better. It should be substantially coated, which is an amount that is sufficient to prevent migration and failure of the taste masking system as a whole.

On the other hand, the seal coating layer cannot add too significantly to the overall size or weight of the API-containing particle. Preferably the seal coating adds less than 15% (±about 30% as noted earlier) to the total weight of the particle when considered against the carrier particle coated with the API-containing layer, more preferably about 10% or less. And while an extremely thin coating is desirable, it may not provide adequate protection. Therefore, in a more preferred embodiment, the seal coating material adds (a minimum of about 2% (±about 30% as noted earlier) and more particularly in a range of between about 5% and about 10% weight gain when compared to the carrier particle coated with the API-containing layer.

The polymers used in the seal coating polymers are themselves dissolved, dispersed or suspended in a solvent, which can be removed or dried without affecting the properties of the coating, the API-containing undercoating or the carrier particle. Again, concentration in the solvent is a secondary factor but it may affect the efficiency of coating and drying.

The coating material may be applied using any technique as previously discussed with the API-containing layer. However, spray coating in a fluidized bed is preferred. After the API-containing layer is applied, as true after each layer, it is preferably dried. Drying can be done as a separate step using any technique or can be accomplished using, for example, a fluidized bed while no new coating material is added. The API coating layer preferably has a moisture content of about 10%, more preferably about 7% or less. After the seal coating layer is applied, it preferably has a moisture or solvent content of about 6% or less.

The materials that may be used for the seal coating layer include, without limitation, hydroxypropylmethylcellulose ("HPMC"), hydroxypropylcellulose, mixtures of both, lactose and HPMC, polydextrose and HPMC, maltodextrin and HPMC, polydextrose, maltodextrin and HPMC, polyvinylacetate carboxymethylcellulose and the like.

The taste masking material useful in accordance with the present invention for producing the taste masking layer generally includes any natural or synthetic polymer including: acrylic polymers, modified celluloses, and the like, which are pH dependant materials that become soluble at a pH of about 6.5 or below, more preferably about 6.0 or below. These polymers and copolymers should preferably be pharmacologically acceptable, capable of providing appropriate release and effective taste masking while still being convenient to process. These include, for example, amino alkyl acrylate copolymers such as, for example, copolymers of methylmethacrylate, butylmethacrylate and dimethylaminoethyl methacrylate. See European Pharmacopoeia 4.4 (04/2003: 1975) at 3385. In one particularly preferred embodiment, the copolymer has a relative molecular mass of about 150,000 and a ratio of dimethylaminoethyl methacrylate groups to butylmethacrylate groups and methylmethacrylate groups of about 2:1:1 and the content of the dimethylaminoethyl groups is about 20.8% to 25.5% based on the amount of dry substances present.

A particularly preferred material can be obtained under the mark Eudragit E-100, which is an acrylated based polymer which dissolves at a pH of about 6.5 or less, and which can be used in normal form or in micronized Eudragit E-100 and mixtures thereof. Eudragit is a trademark of Rohm GmbH, Chemische Fabrik, Kirschenallee, D-64293, Darmstadt, Germany for a group of acrylic polymers.

These materials are generally solid at room temperature. However, they may be applied to the now seal coated and API-coated carrier particle by being dissolved, suspended, emulsified, dispersed or the like in a solvent or solvent system as described previously. Preferred solvents in accordance with the present invention include those capable of substantially dissolving or dispersing Eudragit E-100 such as water, normal $C_1$-$C_5$ alcohol, branched $C_1$-$C_5$ alcohol, denatured $C_1$-$C_5$ alcohol, and low molecular weight ketones such as acetone and MEK. Ethanols, including (SDA-3A) and denatured ethanol are most preferred. Other solvents for the taste masking coating materials include, without limitation, water and those mentioned previously in connection with the seal coating layer.

Generally, the taste masking layer will be provided in an amount ranging from between about 25 to about 55% weight gain as determined by calculating the desired target weight gain over the weight of the carrier particle coated with both the prednisolone salt containing layer and the seal coating layer. (w/w) In a more preferred embodiment the amount ranges from between about 40 to about 50% weight gain. In another embodiment, the range is 35 to 45% target weight gain. The taste masking coating can be applied in the same manner as any other coating described herein including in a preferred embodiment spray coating in a fluidized bed. The taste masked particles are preferably dried to a final moisture content of 5% or less.

The amount of solvent used in forming the taste masking coating will depend on, among other things, the taste masking coating material used. Moreover, more solvent may be needed to achieve dissolution than dispersion, for example. However, since the solvent is generally removed by drying, it should not make up an appreciable portion of the final product, the amount of solvent is not generally considered in describing the overall composition. The taste masking layer may also include anti-tack agents such as magnesium stearate or talc and copolymers such as HPMC, EC, HPC and PVP in an amount of up to about 25% by weight of that coating.

As noted previously, the selection of the seal coating layer and taste masking layer materials and the resulting layers should be coordinated such that the solvents used for the taste masking layer will not adversely affect (compromise its ability to reduce migration across the taste masking layer) the very thin seal coating layer. If both polymer coating materials are water soluble and water is used as the solvent for both, the application of the dissolved, dispersed or suspended taste masking polymer could redissolve and compromise the seal coating, the taste masking coating, or both. Coordination therefore requires consideration of thickness, material, release, and solvent of both coatings.

Indeed, according to the Handbook of Pharmaceutical Excipients, fifth edition, edited by Rowe, Sheskey and Owen and published by the Pharmaceutical Press (copyright 2006) Ethylcellulose cellulose that contains not less than 46.5% of ethoxy groups is freely soluble in 95% ethanol. Id. at 279. Hydroxypropyl methylcellulose (HPMC) is practically insoluble in 95% ethanol. Id. at 347. And Eudragit E 100, also known as poly(butyl methacrylate, (2-dimethylaminoethyl) methacrylate, methyl methacrylate) (1:2:1) (CAS Number [24938-16-7]) lists acetone and alcohols as the recommended solvents. Id. at 555. If one were to use ethylcellulose for a seal coating layer, the use of Eudragit E 100 in an alcohol solution could be problematic. One could choose another solvent for Eudragit E 100, or use HPMC which is practically insoluble in alcohol. The selection of the materials to be used must take into account the other coating materials to be used, what thickness of those materials may be needed to provide the desired performance in terms of release and taste masking, what the coatings will do to the load of API that can be used and the resulting particle size, and what solvents will be necessary and what effect they may have on other layers.

In one embodiment in accordance with the present invention, the seal coating layer has a thickness of about 10 microns or less, preferably about 5 microns or less, and more preferably about 2 microns. The taste masking layer has a thickness of about 50 microns or less, preferably about 40 microns or less, and more preferably about 27 microns.

The tablets of certain embodiments of the invention include an effervescent couple, alone or in combination with other additional ingredients or excipients may be used to improve the disintegration profile and the organoleptic properties of the tablet. Effervescent couples are made from a reaction of a soluble acid source and a metal carbonate or bicarbonate. The acid sources or acid may be any which are safe for human consumption and may generally include food acids, acid anhydrides and acid salts. Food acids include citric acid, tartaric acid, malic acid, fumaric acid, adipic acid, and succinic acids etc. Because these acids are directly ingested, their overall solubility in water is less important than it would be if the effervescent tablet formulations of the present invention were intended to be dissolved in a glass of water. Acid anhydrides and acid salts of the above described acids may also be used. Acid salts may include sodium, dihydrogen phosphate, disodium dihydrogen pyrophosphate, acid citrate salts and sodium acid sulfite.

Carbonate sources include dry solid carbonate and bicarbonate salts such as sodium bicarbonate, sodium carbonate, potassium bicarbonate and potassium carbonate, magnesium carbonate and sodium sesquicarbonate, sodium glycine carbonate, L-lysine carbonate, arginine carbonate and amorphous calcium carbonate. These effervescent couples may be provided in an amount of between about 3% and about 25% by weight of the dosage form.

In addition to and in some instances instead of the effervescence-producing agents, a tablet according to the present invention may also include suitable noneffervescent disintegration agents as an excipient. Nonlimiting examples of noneffervescent disintegration agents include: microcrystalline, cellulose, croscarmellose sodium, crospovidone, starches, corn starch, potato starch and modified starches thereof, clays, such as bentonite, alginates, gums such as agar, guar, locust bean, karaya, pecitin and tragacanth. These noneffervescent disintegrants may comprise up to about 20 weight percent and preferably between about 2% and about 10% of the total weight of the dosage form.

In one embodiment, the invention provides a tablet comprising: rapid release API-containing particles, and an excipient. The API-containing particle comprises a carrier particle coated with an API-containing layer of a prednisolone sodium phosphate present in an amount of about 20 to about 45% by weight of the API-containing particle. The API-containing layer is overcoated with a seal coating layer present in an amount of about 2% to about 15% by weight, and the seal coating layer being overcoated with a taste masking coating layer present in an amount of about 25% to about 55% by weight gain. The API-containing particle being present in an amount of about 55% to about 75% by weight of said tablet. This tablet could be effervescent or could be a non-effervescent tablet. The tablet is preferably an ODT tablet, but it is not necessarily an ODT tablet in accordance with this aspect of the invention. In certain embodiments the tablets of the invention will have a certain hardness, certain friability and/or dissolve/disintegrate in the mouth of a patient with a certain period of time.

The dosage forms (ODT or non-ODT, effervescent or not) may include as additional ingredients or excipients including, without limitation, a noneffervescent disintegration agent as discussed above and/or glidants, fillers, lubricants, binders, sweeteners, flavoring and coloring components. Any conventional sweetener or flavoring component may be used. Combinations of sweeteners, flavoring components, or sweeteners and flavoring components may likewise be used.

Examples of binders which can be used include but are not limited to acacia, tragacanth, gelatin, starch, cellulose materials such as methyl cellulose, microcrystalline cellulose and sodium carboxy methyl cellulose, alginic acids and salts thereof, magnesium aluminum silicate, polyethylene glycol, PVP, guar gum, polysaccharide acids, bentonites, sugars, invert sugars and the like. Binders may be used in an amount of up to 60 weight percent and preferably about 10 to about 40 weight percent of the total dosage form.

Coloring agents may include but are not limited to titanium dioxide, and dyes suitable for food such as those known as F.D.& C. dyes and natural coloring agents such as grape skin extract, beet red powder, beta-carotene, annato, carmine, turmeric, paprika, etc. The amount of coloring used may range from about 0.1 to about 3.5 weight percent of the total dosage form.

Examples of glidants include but are not limited to silicon dioxide, talc, calcium stearate, magnesium stearate, stearowet C, zinc stearate, calcium silicate, starch, pregelatinized starch, magnesium lauryl sulfate, magnesium carbonate, magnesium oxide, and others. These may be used in an amount of between about 0.1 and about 5% by weight of the dosage form.

Diluents or fillers include, but are not limited to spray-dried monohydrate or anhydrous lactose, sucrose, dextrose, mannitol, spray dried mannitol, sugar alcohols, sorbitol, starch, cellulose (e.g., microcrystalline cellulose) dihydrated or anhydrous dibasic calcium phosphate, tricalcium phosphate, maltodextrins, calcium carbonate, calcium sulfate and others. These may be used in an amount of between about 10 and about 90% by weight of the dosage form.

Flavors incorporated in the composition may be chosen from synthetic flavor oils and flavoring aromatics and/or natural oils, extracts from plants, leaves, flowers, fruits and so forth and combinations thereof. These may include cinnamon oil, oil of wintergreen, peppermint oils, clove oil, bay oil, anise oil, eucalyptus, thyme oil, cedar leave oil, oil of nutmeg, oil of sage, oil of bitter almonds and cassia oil. Also useful as flavors are vanilla, citrus oil, including lemon, orange, grape, lime and grapefruit, and fruit essences, including apple, pear, peach, strawberry, raspberry, cherry, plum, pineapple, apricot and so forth. Flavors which have been found to be particularly useful include commercially available orange, grape, cherry and bubble gum flavors and mixtures thereof. The amount of flavoring may depend on a number of factors, including the organoleptic effect desired. Flavors may be present in an amount ranging from about 0.05% to about 3% by weight based upon the weight of the dosage form.

Lubricants may also be used. Hydrophobic lubricants are preferred. Hydrophobic lubricants include, without limitation, calcium stearate, magnesium stearate, zinc stearate, stearic acid, stearowet C, mineral oil, vegetable oil, glyceryl behenate, sodium stearyl fumarate, talc, starch, and others. Hydrophilic lubricants include, without limitation, sodium benzoate, sodium chloride, sodium lauryl sulfate, magnesium lauryl sulfate, polyethylene glycol, and others. Magnesium stearate is preferred. These may be used in an amount of between about 0.5% and about 5% by weight, more preferably 0.5% to about 2.5% by weight of the dosage form. If desired the dosage form may also contain minor amounts of nontoxic substances such as wetting or emulsifying agents, pH buffering agents and the like, for example, sodium acetate, sorbitan monolaurate, triethanolamine, sodium acetate, triethanolamine oleate, sodium lauryl sulfate, dioctyl sodium sulfosuccinate, polyoxyethylene sorbitan fatty acid esters.

Other active pharmaceutical ingredients ("OAPIs") that may be used in accordance with the present invention in addition to a prednisolone salt include, without limitation, analgesics, anti-inflammatories, antipyretics, antibiotics, antimicrobials, anxiolytics, laxatives, anorexics, antihistamines, antidepressants, antiasthmatics, antidiuretics, antiflatuents, antimigraine agents, antispasmodics, sedatives, antihyperactives, antihypertensives, tranquilizers, decongestants, beta blockers, peptides, proteins, oligonucleotides and other substances of biological origin, and combinations thereof. Also contemplated as OAPIs are the drugs and pharmaceutically active ingredients described in Mantelle, U.S. Pat. No. 5,234,957, in columns 18 through 21. That text of Mantelle is hereby incorporated by reference. The above-identified OAPIs may be coated onto the same carrier particle as the prednisolone salt or may be provided in the tablet as a distinct particle. They may be coated or uncoated.

The tablets in accordance with the present invention are tablets which are designed to disintegrate and/or dissolve rapidly in the mouth of a patient once placed in his mouth. By "rapidly," in this context, it is understood that these tablets preferably disintegrate/dissolve in the mouth in less than 120 seconds, more preferably 90 second or less, even more preferably 60 seconds or less, and most preferably 30 seconds. This can be measured by measuring the time it takes of the tablet to dissolve in a test subject's mouth or by using the U.S.P. disintegration method <701> 2006.

In certain embodiments, the tablets of the present invention have a hardness of about 8-20 Newtons, about 8-12 Newtons, about 10-14 Newtons, or about 14-18 Newtons. In one embodiment, the tablets of the present invention have a hardness of about 15 Newtons or more, more preferably 20 Newtons or more, and a friability, as measured by the USP 26th revision (Jan. 1, 2003), at the time of filing, of about 2% or less. In yet another embodiment, these tablets may include at least one non-direct compression carbohydrate (sugar, sugar alcohol, etc.) as a filler. See U.S. Pat. No. 6,024,981. Preferably, these tablets are capable of rapidly disintegrating/dissolving in a patient's mouth in about 60 seconds or less, more preferably about 30 seconds or less, such that the rapid release API-containing particles can be swallowed as a dispersion, suspension or slurry. These tablets may be packaged in blister packages or in openable and reclosable multi-tablet packages.

The tablets of another embodiment of the invention often have a hardness of about 20 Newtons or less, and a friability of more than 2% as measured by the U.S.P. method as of the filing date. Preferably these tablets are capable of rapidly disintegrating/dissolving in a patient's mouth in about 60 seconds or less, more preferably about 30 seconds or less, such that the rapid release API-containing particles can be swallowed as a dispersion, suspension or slurry. Note that while the specification and claims may refer to a tablet of the invention as, for example, containing particles having a certain particle size or distribution, that recitation may be satisfied if the materials used prior to final blending and tablet formulation meet that recitation. In another example, while it might be difficult to know the weight gain of a coated particle or its particle size distribution as it actually exists in the finished tablet, if it is determined that the coated particles used to make the tablet, prior to a final blending and compression step, did exhibit the desired coating level and/or particle size, that is sufficient.

Tablets can either be manufactured by direct compression, wet granulation, dry granulation or any other tablet manufacturing technique. See, e.g., U.S. Pat. Nos. 5,178,878, 5,223, 264 and 6,024,981 which are incorporated by reference herein.

Generally, the process of coating in accordance with the invention proceeds as follows. Spheres, and particularly sugar spheres, are first layered with an API-containing containing layer. In one example, the layering material is a mixture of the API (prednisolone sodium phosphate) in an amount of about 19%, HPMC in an amount of 1%, with the balance being water. The drug is layered to a final potency of 58.8%, i.e., the coated beads include 58.8% of the API by weight. Next the carrier particles containing an API-containing layer can be seal coated with a seal coating material. In one embodiment, the seal coating is made up of 5% HPMC, 9.5% water, with the balance being ethanol. The seal coating layer is applied to a calculated target weight gain of 5% based on the API-containing layer coated carrier particles. The potency of the prednisolone salt, measured based on the weight of the sodium phosphate salt, is now approximately 55.2%. Both of these coatings can be applied by a fluidized bed and can be maintained in the bed for a period of time without additional coating material being added to accomplish some level of drying. The now seal coated particles are coated once again, this time with a taste masking coating. The taste masking coating material can be made, in one example of, 16.7% Eudragit E-100, 8.3% of a lubricant, with the balance of about 75% being ethanol. A calculated 40% w/w target gain is applied, reducing the potency, i.e., the overall content of the API, to about 32.2% by weight of the finished API-containing particles. The particles may be dried, again in the fluidized bed, or in any other way, to a final residual water layer. These materials are then screened, whereafter they can be blended with the effervescent couple and excipients and compressed into tablets. Thereafter they are placed into packages and in particular a preferred embodiment blister packages.

The formulations and tablets of the present invention are useful for treating or preventing any condition for which administration of the API contained therein is considered an appropriate treatment or preventative measure. Thus the present invention includes a method of treating a condition in a subject wherein said condition is treatable with an API. These conditions include, without limitation:

Allergic States

Control of severe or incapacitating allergic conditions intractable to adequate trials of conventional treatment in adult and pediatric populations with: seasonal or perennial allergic rhinitis; asthma; contact dermatitis; atopic dermatitis; serum sickness; drug hypersensitivity reactions.

Dermatologic Diseases

Pemphigus; bullous dermatitis herpetiformis; severe erythema multiforme (Stevens-Johnson syndrome); exfoliative erythroderma; mycosis fungoides.

Edematous States

To induce diuresis or remission of proteinuria in nephrotic syndrome in adults with lupus erythematosus and in adults and pediatric populations, with idiopathic nephrotic syndrome, without uremia.

Endocrine Disorders

Primary or secondary adrenocortical insufficiency (hydrocortisone or cortisone is the first choice; synthetic analogs may be used in conjunction with mineralocorticoids where applicable; in infancy mineralocorticoid supplementation is of particular importance); congenital adrenal hyperplasia; hypercalcemia associated with cancer; nonsuppurative thyroiditis.

Gastrointestinal Diseases

To tide the patient over a critical period of the disease in: ulcerative colitis; regional enteritis Hematologic Disorders Idiopathic thrombocytopenic purpura in adults; selected cases of secondary thrombocytopenia; acquired (autoimmune) hemolytic anemia; pure red cell aplasia; Diamond-Blackfan anemia.

Neoplastic Diseases

For the treatment of acute leukemia and aggressive lymphomas in adults and children.

Nervous System

Acute exacerbations of multiple sclerosis.

Ophthalmic Diseases

Uveitis and ocular inflammatory conditions unresponsive to topical corticosteroids; temporal arteritis; sympathetic ophthalmia.

Respiratory Diseases

Symptomatic sarcoidosis; idiopathic eosinophilic pneumonias; fulminating or disseminated pulmonary tuberculosis when used concurrently with appropriate antituberculous chemotherapy; asthma (as distinct from allergic asthma listed above under "Allergic States"), hypersensitivity pneumonitis, idiopathic pulmonary fibrosis, acute exacerbations of chronic obstructive pulmonary disease (COPD), and Pneumocystis carinii pneumonia (PCP) associated with hypoxemia occurring in an HIV (+) individual who is also under treatment with appropriate anti-PCP antibiotics. Studies support the efficacy of systemic corticosteroids for the treatment of these conditions: allergic bronchopulmonary aspergillosis, idiopathic bronchiolitis obliterans with organizing pneumonia.

Rheumatic Disorders

As adjunctive therapy for short term administration (to tide the patient over an acute episode or exacerbation) in: psoriatic arthritis; rheumatoid arthritis, including juvenile rheumatoid arthritis (selected cases may require low dose maintenance therapy); ankylosing spondylitis; acute and subacute bursitis; acute nonspecific tenosynovitis; acute gouty arthritis; epicondylitis. For the treatment of systemic lupus erythematosus, dermatomyositis (polymyositis), polymyalgia rheumatica, Sjogren's syndrome, relapsing polychondritis, and certain cases of vasculitis.

Miscellaneous

Tuberculous meningitis with subarachnoid block or impending block, tuberculosis with enlarged mediastinal lymph nodes causing respiratory difficulty, and tuberculosis with pleural or pericardial effusion (appropriate antituberculous chemotherapy must be used concurrently when treating any tuberculosis complications); trichinosis with neurologic or myocardial involvement; acute or chronic solid organ rejection (with or without other agents).

This method includes the following steps: administering to the subject an orally disintegrable tablet as described herein comprising placing said orally disintegrable tablet into the mouth of the subject, maintaining the tablet in the mouth of the subject for a time which is sufficient to allow the tablet to disintegrate and/or dissolve, and swallowing the resulting disintegrated and/or dissolved tablet. The formulation used should include an amount of API which is effective to treat or prevent the condition for which it is prescribed or administered. It is also preferred that the orally disintegrable dosage form be in the form of a compressed tablet which can disintegrate in the mouth of a patient within about 60 seconds. In a preferred embodiment, the tablet is placed on top of the tongue and allowed to disintegrate/dissolve and then than swallowed. The patient may be watched for a time sufficient to ensure that the tablet has been dissolved and swallowed.

The tablets of the present invention may be swallowed with water. However, they are preferably orally disintegrable and water need not be taken.

Also contemplated as a separate aspect of the invention are tablets comprising prednisolone sodium phosphate in an amount of about 13.4, about 20.2 or about 40.3 mg and an excipient. These tablets could be, and preferably are effervescent and are made using the twice coated particles as described herein. However, they could be a non-effervescent tablets. They are preferably ODT tablets, but it they are not necessarily ODT tablets in accordance with.

Still another aspect of the invention are tablets comprising prednisolone sodium phosphate and an excipient exhibiting at least one of a log $AUC_{0-t}$ of 2,300 ng·h/mL±600, a log $AUC_{inf}$ of 2,300 ng·h/mL±600, a log $C_{max}$ of 400 ng/ml±100 or a $t_{max}$ of 1.3 hours±20 mins.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

DETAILED DESCRIPTION OF THE PREFERRED EMBODIMENTS

Example 1

Effervescent ODT tablets, as described below in Table 1, may be made using the 32.2% API-containing particles described above using the following common blend formulation.

TABLE 1

| Component | Quantity (mg/g) |
|---|---|
| Coated prednisolone sodium phosphase (32.2%) based on salt | 219.6[a] |
| Mannitol EZ, USP | 295.4[b] |
| Mannitol, USP/EP/JP | 250.0 |
| Crospovidone, NF/EP/JP | 100.0 |
| Microcrystalline cellulose, NF/EP/JP | 30.0 |
| Sodium bicarbonate, USP/EP/JP | 28.0 |
| Citric acid, USP/EP/JP | 22.0 |
| Flavor | 20.0 |
| Magnesium stearate, NF/EP/JP | 20.0 |
| Micronized sucralose powder, NF | 10.0 |
| Colloidal silicon dioxide, NF/EP | 5.0 |
| TOTAL | 1000.00 |

[a]actual amount is based on Coated PSP beads assay
[b]actual amount adjusted based on the Coated beads amount Prednisolone ODT™ formulations 10 mg, 15 mg or 30 mg of prednisolone free base (administered as 13.4, 20.2, or 40.3 mg of prednisolone sodium phosphate respectively) can be produced as follows. The three tablet strengths can be made compositionally proportional i.e. a common final blend is manufactured and compressed into 10 mg, 15 mg or 30 mg tablets. The common blend is a mixture of Coated PSP, Mannitol, Mannitol EZ, Crospovidone, Microcrystalline Cellulose, Sucralose, Sodium Bicarbonate, Citric Acid, Grape flavor, Colloidal Silicon Dioxide and Magnesium Stearate as discussed above. The manufacturing process uses conventional blending and compression equipment. The manufacturing process uses conventional diffusion-type blending followed by compression and blister packaging. The Prednisolone ODT™ tablets are packaged in unit dose blisters (one tablet per blister cavity). The blister forming film consists of a four layer laminate material composed of polyvinyl chloride (PVC) film/oriented polyamide (OPA) film/aluminum foil/polyvinyl chloride (PVC) film. The blister forming film is heat sealed with a lidding material composed of paper/polyester film/aluminum foil/heat seal coating. The product contact surfaces of the cold form blister foil and lidding are the polyvinyl chloride (PVC) film and the heat seal coating respectively. Tablets can be produced meeting the following criteria listed in Table 2 below.

TABLE 2

| Prednisolone Dose (mg) | PSP dose (mg) | Tablet Size | Tablet Wt (mg) | Shape | Color | Hardness (N) | Thickness Range (inches) |
|---|---|---|---|---|---|---|---|
| 10 | 13.4 | 5/16" | 190 | Round Flat Faced | White | 8–12 (Target = 10) | 0.139–0.140 |
| 15 | 20.2 | 3/8" | 285 | Round Flat Faced | White | 10–14 (Target = 12) | 0.147–0.149 |
| 30 | 40.3 | 1/2" | 570 | Round Flat Faced | White | 14–18 (Target = 16) | 0.164–0.166 |

Example 2

The procedure for manufacturing of Orapred™ ODT tablets in accordance with the invention include the following steps:

1. Drug is layered over an inert material (sugar beads).
2. Layered beads are seal-coated.
3. Layered/seal-coated beads are coated again (taste masking step).
4. Prednisolone sodium phosphate (PSP) tablets undergo weigh/blend process to adjust weight based on final potency value to be used for tablet blend.
5. Final blend is compressed using rotary tablet press.
6. Tablets are packaged into foil/foil blisters using appropriate packaging materials and equipment.

Provided below in Table 3 (formula for 32.2% Coated Prednisolone Sodium Phosphate) and Table 4 (formula for the 40.3 mg Prednisolone Phosphate ODTs).

TABLE 3

Coated Prednisolone Sodium Phosphate, 32.2%

| Component Description | Reference | Function | Wt. Per 30 mg tablet |
|---|---|---|---|
| Prednisolone Sodium Phosphate | USP | Active | 40.3 mg |
| Sugar Spheres, NF (60/80)b | NF | Inert material | 27.03 mg |

TABLE 3-continued

Coated Prednisolone Sodium Phosphate, 32.2%

| Component Description | Reference | Function | Wt. Per 30 mg tablet |
|---|---|---|---|
| Hypromellose 2910, USP | USP | Binder | 6.11 mg |
| Eudragit ® E-100, EP/JPE | EP/JPE | Taste masking agent | 33.39 mg |
| Magnesium Sterate, NF/EP/JP | NF/EP/JP | Lubricant | 16.67 mg |
| Purified Water, USP | USP | Solvent | * |
| Alcohol, SDA-3A, Anhydrous | USP | Solvent | * |

* Removed during processing.

Orapred ODT 30 mg prednisolone base equivalent tablet is a white, flat faced, beveled edge tablet with debossing "ORA" on one side and "30" on the other.

TABLE 4

Tablet formula for Orapred ODT 30 mg Tablets (Equivalent to Prednisolone Sodium Phosphate 40.3 mg)

| COMPONENT NAME | Reference | Function | Quantity (mg/30 mg tablet) |
|---|---|---|---|
| Coated Prednisolone Sodium Phosphate (32.2%) | | Active | 125.16[a,b] |
| Mannitol EZ | USP/EP/JP | Diluent | 168.39[c] |
| Mannitol | USP/EP/JP | Diluent | 142.50 |
| Crospovidone | NF/EP/JP | Disintegrant | 57.00 |
| Microcrystalline Cellulose[d] | NF/EP/JP | Diluent | 17.10 |
| Sodium Bicarbonate | USP/EP/JP | Effervescent | 16.00 |
| Citric Acid | USP/EP/JP | Effervescent | 12.50 |
| Grape Flavor SN054158 | | Flavor | 11.40 |
| Magnesium Stearate | NF/EP/JP | Lubricant | 11.40 |
| Micronized Sucralose Powder | NF | Sweetener | 5.70 |
| Colloidal Silicon Dioxide | NF/EP | Glidant | 2.85 |
| Total | | | 570.00 |

*Route; dosage form is oral; tablet, orally disintegrating
***Route; dosage form is oral; tablet
[a]Actual amount is based on Coated PSP assay
[b]Equivalent to 40.3 mg of Prednisolone Sodium Phosphate or 30 mg prednisolone base
[c]Actual amount adjusted based on the Coated PSP amount
[d]Avicel PH 113

The tablets were made following the tableting procedure explained in Example 1.

The invention claimed is:

1. An orally disintegrating tablet comprising:
    a) a plurality of rapid release taste masked particles wherein the rapid release taste masked particles comprise:
        i) a core comprising a carrier particle and prednisolone sodium phosphate wherein the prednisolone sodium phosphate comprises about 20% to about 45% by weight of the rapid release taste masked particles;
        ii) a seal coating surrounding the core wherein the seal coating comprises about 2% to about 15% by weight of the rapid release taste masked particles; and
        iii) a taste masking coating surrounding the seal coating comprising a polymer that is soluble below a pH of about 6.5, and
    wherein the taste masking coating comprises about 25% to about 55% by weight of the rapid release taste masked particles,
    wherein at least 90% of the rapid release taste masked particles pass through a 30 mesh screen and not less than 60% of the rapid release taste masked particles are retained on a 60 mesh screen and the rapid release taste masked particles have a total moisture content of less than 5% by weight of the rapid release taste masked particles,
    b) about 3% to about 25% by weight of the tablet of an effervescent couple;
    c) about 2% to about 20% by weight of the tablet of a noneffervescent disintegrant selected from the group consisting of microcrystalline cellulose, croscarmellose sodium, crospovidone, alginates, starches such as corn starch, potato starch and modified starches thereof, gums such as agar and guar, and combinations thereof; and
    d) at least one excipient selected from the group consisting of a filler, a binder, a flavor, a color, a lubricant, a glidant and a pH adjusting agent, and
    wherein the tablet has a moisture content of 5% or less by weight of the tablet, and disintegrates in a patient's mouth in 60 seconds or less to provide a suspension or slurry of the rapid release taste masked particles which can be swallowed.

2. The orally disintegrating tablet as defined in claim 1 wherein the moisture content of the tablet is 4% or less by weight of the tablet.

3. The orally disintegrating tablet as defined in claim 2 wherein the moisture content of the tablet is 3% or less by weight of the tablet.

4. The orally disintegrating tablet as defined in claim 1 wherein the seal coating comprises hydroxypropylmethylcellulose, hydroxypropyl cellulose, lactose, polydextrose, maltodextrin, polyvinylacetate or carboxymethylcellulose.

5. The orally disintegrating tablet as defined in claim 1 wherein the polymer is an amino alkyl acrylate copolymer.

6. The orally disintegrating tablet as defined in claim 1 wherein the prednisolone sodium phosphate comprises about 29% to about 36% of the weight of the rapid release taste masked particles.

7. The orally disintegrating tablet as defined in claim 1 wherein the seal coating comprises about 5% to about 10% of the weight of the rapid release taste masked particles.

8. The orally disintegrating tablet as defined in claim 1 wherein the prednisolone sodium phosphate comprises about 31% to about 34% of the weight of the rapid release taste masked particles.

9. The orally disintegrating tablet as defined in claim 1 wherein not less than 65% of the rapid release taste masked particles are retained on a 60 mesh screen.

10. An orally disintegrating tablet comprising:
    a) a plurality of rapid release taste masked particles wherein the rapid release taste masked particles comprise:
        i) a core comprising an inert sugar sphere, prednisolone sodium phosphate and a binder, wherein the prednisolone sodium phosphate comprises about 20% to about 45% by weight of the rapid release taste masked particles;
        ii) a seal coating surrounding the core wherein the seal coating comprises about 2% to about 15% by weight of the rapid release taste masked particles; and iii) a taste masking coating surrounding the seal coating comprising a polymer that is soluble below a pH of about 6.5 and a binder, and wherein the taste masking coating comprises about 25% to about 55% by weight of the rapid release taste masked particles, wherein at least 90% of the rapid release taste masked particles pass through a 30 mesh screen and not less than 60% of the rapid release taste masked particles are retained on a 60 mesh screen and the rapid release taste masked particles have a total moisture content of less than 5% by weight of the rapid release taste masked particles, b) about 3% to about 25% by weight of the tablet of an effervescent couple; and c) about 10% to about 90% by weight of the tablet of a filler;

d) about 2% to about 20% by weight of the tablet of a noneffervescent disintegrant selected from the group consisting of microcrystalline cellulose, croscarmellose sodium, crospovidone, alginates, starches such as corn starch, potato starch and modified starches thereof, gums such as agar and guar, and combinations thereof;

e) about 0.05% to about 3% by weight of the tablet of a flavor;

f) about 0.5% to about 5% by weight of the tablet of a lubricant;

g) about 0.1% to about 5% by weight of the tablet of a glidant; and wherein the tablet has a moisture content of 5% or less by weight of the tablet, and disintegrates in a patient's mouth in 60 seconds or less to provide a suspension or slurry of the rapid release taste masked particles which can be swallowed.

* * * * *